(12) United States Patent
Kubis et al.

(10) Patent No.: US 11,508,463 B2
(45) Date of Patent: Nov. 22, 2022

(54) METHOD OF IDENTIFYING PROPERTIES OF MOLECULES UNDER OPEN BOUNDARY CONDITIONS

(71) Applicant: PURDUE RESEARCH FOUNDATION, West Lafayette, IN (US)

(72) Inventors: Tillmann Kubis, West Lafayette, IN (US); James Charles, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 140 days.

(21) Appl. No.: 16/624,833

(22) PCT Filed: Jun. 29, 2018

(86) PCT No.: PCT/US2018/040348
§ 371 (c)(1),
(2) Date: Dec. 19, 2019

(87) PCT Pub. No.: WO2019/006340
PCT Pub. Date: Jan. 3, 2019

(65) Prior Publication Data
US 2020/0126638 A1 Apr. 23, 2020

Related U.S. Application Data

(60) Provisional application No. 62/526,470, filed on Jun. 29, 2017.

(51) Int. Cl.
*G16C 10/00* (2019.01)
*G16C 20/30* (2019.01)
(Continued)

(52) U.S. Cl.
CPC ............. *G16C 10/00* (2019.02); *G06F 17/18* (2013.01); *G06F 30/28* (2020.01); *G16C 20/30* (2019.02);
(Continued)

(58) Field of Classification Search
CPC ......... G16C 10/00; G16C 20/30; G06F 30/28; G06F 17/18; G06F 2113/08; G06F 2111/10
See application file for complete search history.

(56) References Cited

U.S. PATENT DOCUMENTS 5,260,882 A 11/1993 Biacco et al.
7,702,467 B2 4/2010 Duffy
(Continued)

FOREIGN PATENT DOCUMENTS

EP 3040889 A1 * 7/2016 ............. G16C 20/30
WO 2005122052 A1 12/2005

OTHER PUBLICATIONS

Bernholc, Jerzy, Miroslav Hodak, and Wenchang Lu. "Recent developments and applications of the real-space multigrid method." (IOP Publishing Ltd., 2008) Journal of Physics: Condensed Matter 20, No. 29: 294205. doi:10.1088/0953-8984/20/29/294205 (Year: 2008).*

(Continued)

*Primary Examiner* — Rehana Perveen
*Assistant Examiner* — Daniel E Miller
(74) *Attorney, Agent, or Firm* — Maginot, Moore & Beck LLP

(57) ABSTRACT

A method of determining at least one property of a liquid system using a modeling system, the liquid system including at least one molecule in a solvent, the modeling system including a processor, comprises generating a quantum model of the liquid system using the processor of the (Continued)

modeling system, the quantum model including a device region and a lead region, the device region being spherical, paraboloid, cubic or arbitrary in shape and encompassing the at least one molecule and a portion of the solvent of the liquid system, the lead region encompassing a region of the solvent surrounding the device region, determining a first property of the device region by solving a first quantum equation for the device region using the processor of the system, determining the first property of the lead region by solving the first quantum equation under open boundary conditions for the lead region using the processor of the system, and combining the first property of the device region with the first property of the lead region to arrive at a total first property for the liquid system using the processor of the system.

12 Claims, 4 Drawing Sheets

(51) Int. Cl.
  *G06F 30/28* (2020.01)
  *G06F 17/18* (2006.01)
  *G06F 113/08* (2020.01)
  *G06F 111/10* (2020.01)

(52) U.S. Cl.
  CPC ....... *G06F 2111/10* (2020.01); *G06F 2113/08* (2020.01)

(56) References Cited

U.S. PATENT DOCUMENTS

| 2005/0015422 | A1 | 1/2005 | Kohn et al. | |
| 2007/0177437 | A1* | 8/2007 | Guo | B82Y 10/00 365/189.07 |
| 2008/0147360 | A1 | 6/2008 | Fejes et al. | |

OTHER PUBLICATIONS

Malaspina, Thaciana, Eudes E. Fileti, and Roberto Rivelino. "Structure and UV-vis spectrum of C60 fullerene in ethanol: a sequential molecular dynamics/quantum mechanics study." (American Chemical Society, 2007) The Journal of Physical Chemistry B 111, No. 41: 11935-11939. (Year: 2007).*
Li, Xiantao, Lin Lin, and Jianfeng Lu. "PEXSI-$\Sigma $: A Green's function embedding method for Kohn-Sham density functional theory." (arXivLabs, 2016) arXiv preprint arXiv:1606.00515 [physics.comp-ph]. [Retrieved online] <https://arxiv.org/abs/1606.00515>. (Year: 2016).*
Gruebele, Martin. "Quantum dynamics and control of vibrational dephasing." (IOP Publishing Ltd., 2004) Journal of Physics: Condensed Matter 16, No. 30 (2004): R1057. doi:10.1088/0953-8984/16/30/R02 (Year: 2004).*
Canuto, Sylvio, ed. Solvation effects on molecules and biomolecules: computational methods and applications. (Springer Science & Business Media, 2010) vol. 6. p. 14. ISBN: 978-1-4020-8269-6 (Year: 2010).*
Lent, Craig S., and David J. Kirkner. "The quantum transmitting boundary method." (American Institute of Physics, 1990) Journal of Applied Physics 67, No. 10 pp. 6353-6359. (Year: 1990).*
Steiger, Sebastian, Michael Povolotskyi, Hong-Hyun Park, Tillmann Kubis, and Gerhard Klimeck. "NEMO5: A parallel multiscale nanoelectronics modeling tool." (IEEE, 2011) IEEE Transactions on Nanotechnology 10, No. 6 pp. 1464-1474. (Year: 2011).*
Hodak, Miroslav, Wenchang Lu, and J. Bernholc. "Hybrid ab initio Kohn-Sham density functional theory/frozen-density orbital-free density functional theory simulation method suitable for biological systems." (AIP, 2008) The Journal of chemical physics 128, No. 101B601. pp. 14101-1-14101-9. (Year: 2009).*
Li, H., and G. Li. "Analysis of ballistic transport in nanoscale devices by using an accelerated finite element contact block reduction approach." (AIP, 2014) Journal of Applied Physics 116, No. 8 pp. 084501-1-084501-13. (Year: 2014).*
M. J. Gillan, D. Alfe, and A. Michaelides, "Perspective: How good is dft for water?" The Journal of chemical physics, vol. 144, No. 13, p. 130901, 2016.
B. J. Alder and T. E. Wainwright, "Studies in molecular dynamics. i. general method," The Journal of Chemical Physics, vol. 31, No. 2, pp. 459-466, 1959.
P. L. Freddolino and K. Schulten, "Common structural transitions in explicit solvent simulations of villin headpiece folding," Biophysical journal, vol. 97, No. 8, pp. 2338-2347, 2009.
N. Sergueev, D. Roubtsov, and H. Guo, "Ab initio calculation of transport properties of metal-c60-metal junctions," arXiv preprint cond-mat/0309614, 2003.
K. Moth-Poulsen and T. Bjørnholm, "Molecular electronics with single molecules in solid-state devices," Nature nanotechnology, vol. 4, No. 9, pp. 551-556, 2009.
T. Kubis, Y. He, R. Andrawis, and G. Klimeck, "General retarded contact self-energies in and beyond the non-equilibrium green's functions method," in Journal of Physics: Conference Series, vol. 696, No. 1. IOP Publishing, 2016, p. 012019.
Nirmalraj, P. "Fingerprinting electronic molecular complexes in liquid," Scientific reports, 2016, vol. 6.
N. Marzari and D. Vanderbilt, "Maximally localized generalized wannier functions for composite energy bands," Physical review B, 1997, vol. 56, No. 20, p. 12847.
Svizhenko, A. et al., Two-Dimensional Quantum Mechanical Modeling of Nanotransistors, Journal of Applied Physics, 2002, vol. 91, No. 4.
Dror, Ron. Molecular dynamics simulation, CS/CME/BioE/Biophys/BMI 279, 2019.
Software for the simulation of electronic and optoelectronic semiconductor nanodevices, nextnano.com, 2019.
Quantum espresso. [Online]. Available: http://www.quantum-espresso.org/, 2019.
Kresse, Georg, VASP the Guide, Computational Materials Physics, Faculty of Physics, Universit at Wien, Sensengasse 8/12, A-1090 Wien, Austria, 2018.
M. F. Frasco and N. Chaniotakis, "Semiconductor quantum dots in chemical sensors and biosensors," Sensors, vol. 9, No. 9, pp. 7266-7286, 2009.
T. Ando, "Screening effect and quantum transport in a silicon inversion layer in strong magnetic fields," Journal of the Physical Society of Japan, vol. 43, No. 5, pp. 1616-1626, 1977.
S. Kim, A. Konar, W.-S. Hwang, J. H. Lee, J. Lee, J. Yang, C. Jung, H. Kim, J.-B. Yoo, J.-Y. Choi et al., "High-mobility and low-power thin-film transistors based on multilayer mos2 crystals," Nature communications, vol. 3, p. 1011, 2012.
T. Kubis, "Quantum transport in semiconductor nanostructures," Ph.D. dissertation, Verein zur Frderung des Walter Schottky Instituts der Technischen Universitat Munchen e.V., Garching, 2009.
M. C. Dharma-wardana, "Current issues in finite-t density-functional theory and warm-correlated matter," Computation, vol. 4, No. 2, p. 16, 2016.
P. Stephens, F. Devlin, C. Chabalowski, and M. J. Frisch, "Ab initio calculation of vibrational absorption and circular dichroism spectra using density functional force fields," The Journal of Physical Chemistry, vol. 98, No. 45, pp. 11 623-11 627, 1994.
K. Laasonen, M. Sprik, M. Parrinello, and R. Car, "ab initioliquid water," The Journal of chemical physics, vol. 99, No. 11, pp. 9080-9089, 1993.
J. Winkelmann, U. Brodrecht, and I. Kreft, "Density functional theory: Modelling of surface tensions for molecular fluids," Berichte der Bunsengesellschaft fur physikalische Chemie, vol. 98, No. 7, pp. 912-919, 1994.
S. Datta, "Nanoscale device modeling: the greens function method," Superlattices and Microstructures, vol. 28, No. 4, pp. 253-278, 2000.

(56) References Cited

OTHER PUBLICATIONS

R. Lake, G. Klimeck, R. C. Bowen, and D. Jovanovic, Journal of Applied Physics, vol. 81, No. 12, pp. 7845-7869, 1997.
T. Kubis, PhD thesis, Verein zur Förderung des Walter Schottky Instituts der Technischen Universitat München e.V., Garching, 2009.
M. Luisier and G. Klimeck, Journal of Applied Physics, vol. 107, No. 8, p. 084507, 2010.
M. Luisier and G. Klimeck, Physical Review B, vol. 80, No. 15 155430, 2009.
M. Anantram, M. S. Lundstrom, and D. E. Nikonov, Proceedings of the IEEE, vol. 96, No. 9, pp. 1511-1550, 2008.
Krishnamoorthy, A., Menon, D., IEEE, pp. 70-72, 2013.
J. Taylor, H. Guo, and J. Wang, "Ab initio modeling of quantum transport properties of molecular electronic devices," Physical Review B, vol. 63, No. 24, p. 245407, 2001.
S. Sadasivam, Y. Che, Z. Huang, L. Chen, S. Kumar, and T. S. Fisher, "The atomistic greens function method for interfacial phonon transport," Ann. Rev. Heat Transfer, vol. 17, pp. 89-145, 2014.
S. Steiger, R. G. Veprek, and B. Witzigmann, "Electroluminescence from a quantum-well led using negf," in Computational Electronics, 2009. IWCE'09. 13th International Workshop on. IEEE, 2009, pp. 1-4.
D. A. Stewart and F. Leonard, "Energy conversion efficiency in nanotube optoelectronics," Nano letters, vol. 5, No. 2, pp. 219-222, 2005.
J. Schwinger, "Brownian motion of a quantum oscillator," Journal of Mathematical Physics, vol. 2, No. 3, pp. 407-432, 1961.
S. Fujita, "Partial self-energy parts of kadanoff-baym," Physica, vol. 30, No. 4, pp. 848-856, 1964.
S.M. Goodnick, D. K. Ferry, C. Wilmsen, Z. Liliental, D. Fathy, and O. Krivanek, "Surface roughness at the si (100)-sio 2 interface," Physical Review B, vol. 32, No. 12, p. 8171, 1985.
M. R. Amirzada, A. Tatzel, V. Viereck, and H. Hillmer, "Surface roughness analysis of sio2 for pecvd, pvd and ibd on different substrates," Applied Nanoscience, pp. 1-8, 2015.
S. Jin, M. V. Fischetti, and T.-W. Tang, "Modeling of surface-roughness scattering in ultrathin-body soi mosfets," Electron Devices, IEEE Transactions on, vol. 54, No. 9, pp. 2191-2203, 2007.
S. R. Mehrotra, A. Paul, and G. Klimeck, "Atomistic approach to alloy scattering in si1-xgex," Applied Physics Letters, vol. 98, No. 17, p. 173503, 2011.
A. Esposito, M. Frey, and A. Schenk, "Quantum transport including nonparabolicity and phonon scattering: application to silicon nanowires," Journal of computational electronics, vol. 8, No. 3-4, pp. 336-348, 2009.
M. Luisier and G. Klimeck, "Atomistic full-band simulations of silicon nanowire transistors: Effects of electron-phonon scattering," Physical Review B, vol. 80, No. 15, p. 155430, 2009.
M. A. Khayer and R. K. Lake, "Effects of band-tails on the subthreshold characteristics of nanowire band-to-band tunneling transistors," Journal of Applied Physics, vol. 110, No. 7, p. 074508, 2011.
J. Charles, P. Sarangapani, R. Golizadeh-Mojarad, R. Andrawis, D. Lemus, X. Guo, D. Mejia, J. E. Fonseca, M. Povolotskyi, T. Kubis et al., "Incoherent transport in nemo5: realistic and efficient scattering on phonons," Journal of Computational Electronics, pp. 1-7, 2016.
S. Karpov, "Abc-model for interpretation of internal quantum efficiency and its droop in iii-nitride leds: a review," Optical and Quantum Electronics, vol. 47, No. 6, pp. 1293-1303, 2015.
W. Scheibenzuber, U. Schwarz, L. Sulmoni, J. Dorsaz, J.-F. Carlin, and N. Grandjean, "Recombination coefficients of gan-based laser diodes," Journal of Applied Physics, vol. 109, No. 9, p. 093106, 2011.
J. Piprek, "Efficiency droop in nitride-based light-emitting diodes," physica status solidi (a), vol. 207, No. 10, pp. 2217-2225, 2010.
S. Zeng, S. Hu, J. Xia, T. Anderson, X.-Q. Dinh, X.-M. Meng, P. Coquet, and K.-T. Yong, "Graphene-mos 2 hybrid nanostructures enhanced surface plasmon resonance biosensors," Sensors and Actuators B: Chemical, vol. 207, pp. 801-810, 2015.
T. Kubis and P. Vogl, "Assessment of approximations in nonequilibrium greens function theory," Physical Review B, vol. 83, No. 19, p. 195304, 2011.
B. C. Doak, R. S. Norton, and M. J. Scanlon, "The ways and means of fragment based drug design," Pharmacology & Therapeutics, vol. 167, pp. 28-37, 2016.
A. Dreuw, J. L. Weisman, and M. Head-Gordon, "Long-range charge-transfer excited states in time-dependent density functional theory require non-local exchange," The Journal of chemical physics, vol. 119, No. 6, pp. 2943-2946, 2003.
A. C. Van Duin, S. Dasgupta, F. Lorant, and W. A. Goddard, "Reaxff: a reactive force field for hydrocarbons," The Journal of Physical Chemistry A, vol. 105, No. 41, pp. 9396-9409, 2001.
W. Kohn, A. D. Becke, and R. G. Parr, "Density functional theory of electronic structure," The Journal of Physical Chemistry, vol. 100, No. 31, pp. 12 974-12 980, 1996.
T. Klaver, G. Madsen, and R. Drautz, "A dft study of formation energies of fe—zn—al intermetallics and solutes," Intermetallics, vol. 31, pp. 137-144, 2012.
M. J. Spencer, A. Hung, I. K. Snook, and I. Yarovsky, "Density functional theory study of the relaxation and energy of iron surfaces," Surface Science, vol. 513, No. 2, pp. 389-398, 2002.
J. Autschbach and T. Ziegler, "Calculating molecular electric and magnetic properties from time-dependent density functional response theory," The Journal of chemical physics, vol. 116, No. 3, pp. 891-896, 2002.
A. K. Mishra, A. Roldan, and N. H. de Leeuw, "A density functional theory study of the adsorption behaviour of co2 on cu2o surfaces," The Journal of Chemical Physics, vol. 145, No. 4, p. 044709, 2016.
A. Pribram-Jones, S. Pittalis, E. Gross, and K. Burke, "Thermal density functional theory in context," in Frontiers and Challenges in Warm Dense Matter. Springer, 2014, pp. 25-60.
F. Furche and R. Ahlrichs, "Adiabatic time-dependent density functional methods for excited state properties," The Journal of chemical physics, vol. 117, No. 16, pp. 7433-7447, 2002.
S. S. Leang, F. Zahariev, and M. S. Gordon, "Benchmarking the performance of time-dependent density functional methods," The Journal of chemical physics, vol. 136, No. 10, p. 104101, 2012.
S. Chibani, B. Le Guennic, A. Charaf-Eddin, O. Maury, C. Andraud, and D. Jacquemin, "On the computation of adiabatic energies in aza-borondipyrromethene dyes," Journal of chemical theory and computation, vol. 8, No. 9, pp. 3303-3313, 2012.
A. Dreuw and M. Head-Gordon, "Failure of time-dependent density functional theory for long-range charge-transfer excited states: the zinc bacteriochlorinbacteriochlorin and bacteriochlorophyll-spheroidene complexes," Journal of the American Chemical Society, vol. 126, No. 12, pp. 4007-4016, 2004.
C. Adamo and D. Jacquemin, "The calculations of excited-state properties with time-dependent density functional theory," Chemical Society Reviews, vol. 42, No. 3, pp. 845-856, 2013.

* cited by examiner

METHOD OF IDENTIFYING PROPERTIES OF MOLECULES UNDER OPEN BOUNDARY CONDITIONS

CROSS-REFERENCE TO RELATED APPLICATIONS

This application claims priority to U.S. Provisional Application Ser. No. 62/526,470 entitled "METHOD OF COMPUTING ELECTRONIC PROPERTIES" by Charles et al., filed 29 Jun. 2017, the disclosure of which is hereby incorporated herein by reference in its entirety.

TECHNICAL FIELD

The present invention is related to the field of molecular modeling, and, more particularly, to the use of molecular models to identify quantum properties of molecules in liquid systems.

BACKGROUND

An accurate simulation of the properties and/or behavior of a liquid system, such as a molecule or molecules in a solvent, needs to account for the effects of the bulk medium, or "solvent", which provides the environment for the molecule of interest. The solvent is typically an aqueous liquid (e.g., water) although it may comprise hydrophobic membranes, other organic or inorganic molecules, emulsions, solids, alloys or mixtures of the above. Important solvent properties include electrostatic screening, cavitation effects, pH, local interactions with other molecules, viscosity, and the provision of a constant-temperature environment. Some or all the solvent's properties may vary spatially. Temporal changes in solvent properties, such as temperature changes, may also occur.

Liquid systems are inherently open quantum systems. In previously known quantum models of open systems, the system is considered as a device connected between two contacts, namely source and drain contacts. The open boundary condition of the system was taken into account by contact self-energies, which represent the charge injection and extraction effect of the contacts. After the contact self-energies are solved, the electronic transport of the system is solved by either non-equilibrium Green's function (NEGF) methods or quantum transmitting boundary method (QTBM) algorithms.

While such previously known methods are effective, the source and drain contacts, which define how the system interacts with the surrounding environment, are finite or semi-finite constructs. In contrast, the contacts/leads of an open system under open boundary conditions are theoretically infinite and extend in all directions. Consequently, the source and drain contacts used in previously known modeling methods do not fully represent an open system under open boundary conditions.

DETAILED DESCRIPTION

Figure 1:
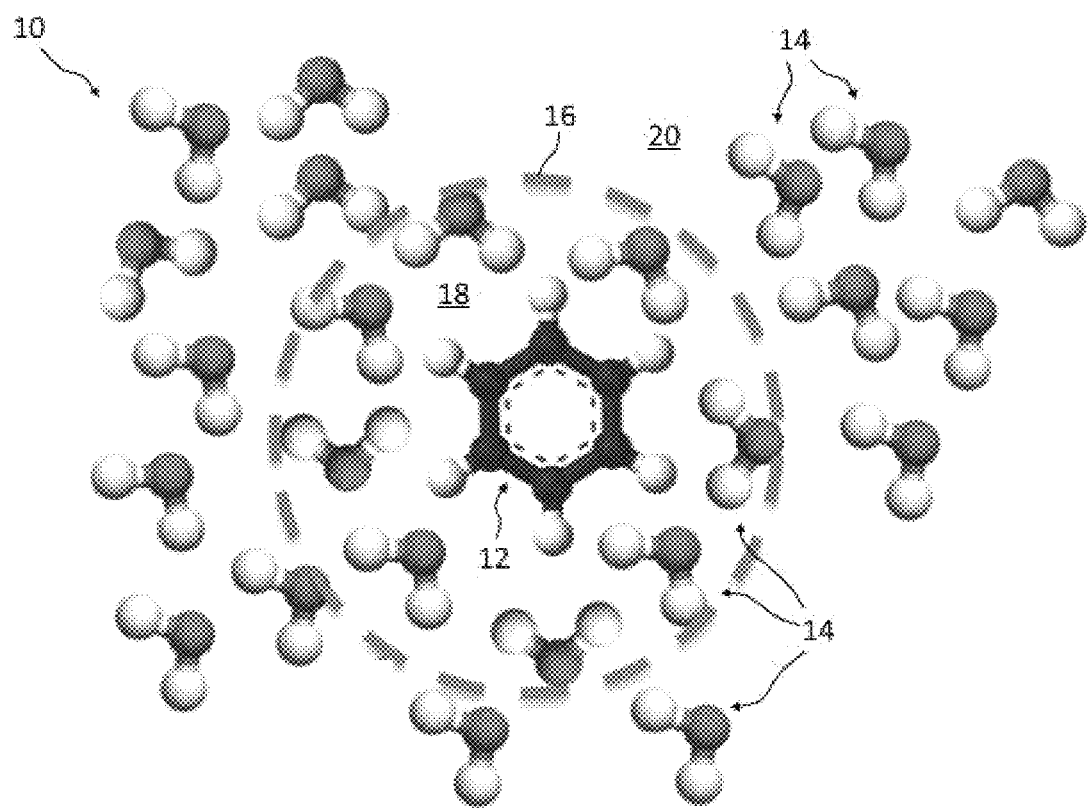
FIG. 1 depicts a schematic diagram of an embodiment of a liquid system that is modeled using the modeling system and methods of the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to a person of ordinary skill in the art to which this disclosure pertains.

The present disclosure is directed to methods and systems for modeling a liquid (e.g., molecule/solvent) system that enables the quantum mechanical behavior of the system to be analyzed under open boundary conditions. The model enables open system quantum properties to be calculated for the liquid system. Any kind of observable property may be identified for the liquid system using the model, including density, solubility, reactivity, stability, optical spectra, thermal spectra, magnetic properties, susceptibility, and the like. The model according to the present disclosure is capable of handling any-dimensional open quantum boundary conditions accurately. There is no way currently known to solve open quantum boundaries in three dimensions. All existing methods have only finite-area quantum leads.

A schematic diagram 10 of a liquid system comprising a molecule 12 in a solvent 14 is depicted in FIG. 1. As used herein, the singular term "molecule" will be used to encompass whatever atomic structure that is to be modeled in the solvent, which can be one or more atoms, one or more molecules, atomic chain(s), solute, and the like. The molecule depicted in the schematic diagram of FIG. 1 is a benzene ($C_6H_6$) and the solvent is water. In alternative embodiments, similar models may be generated for substantially any type of molecule in substantially any type of solvent.

Figure 2:
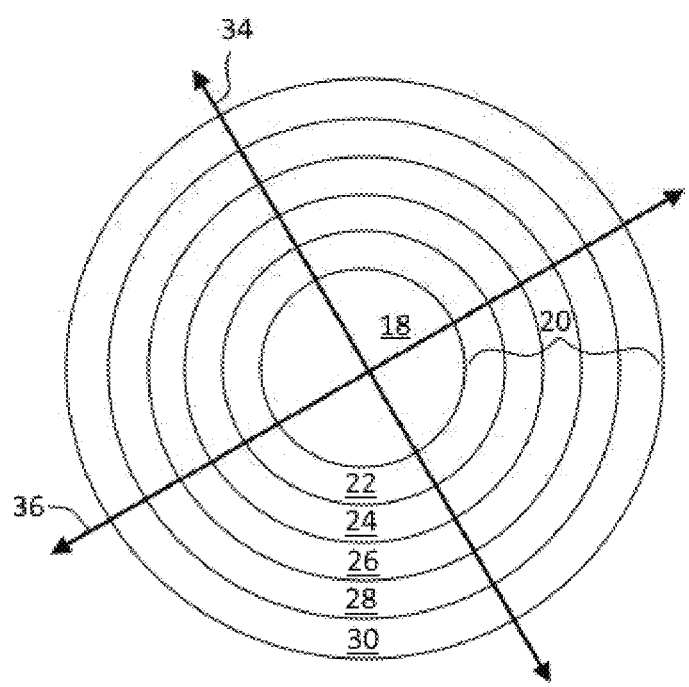
FIG. 2 depicts an embodiment of a model that may be used to model the liquid system of FIG. 1 under open quantum liquid boundary conditions.

In accordance with the present disclosure, a quantum model of a liquid system, such as the system depicted in FIG. 1, is generated using a suitable simulation/modeling system. An example of such a system is NEMO5. FIG. 2 depicts one embodiment of a quantum model which may be used to model the system of FIG. 1. The liquid system is considered an open system. To model as an open system, the device region is considered as a three-dimensionally shaped region that encompasses the molecule of the liquid system and a portion of the solvent immediately surrounding the molecule.

The model also includes a lead region. As noted above, the lead region was modeled as two contacts, i.e., source and drain contacts, connected to a device in previously known methods which are finite or semi-finite in area and therefore not truly representative of a system under open boundary conditions.

As an alternative to modeling the systems interaction with the surrounding environment using finite or semi-finite leads (e.g., source and drain contacts), the lead region is considered as three-dimensionally shaped region that completely surrounds the device region and has a shape that matches the outer shape of the device region. This configuration for the lead region enables the leads for the device to be handled as being infinite and extending in all directions from the device which is a more accurate representation of the open boundary conditions of an open system, such as a liquid system.

Modeling the liquid system begins with the selection of a base shape for the model which will define the shape of the device region as well as surrounding lead region. Any suitable three-dimensional shape may be used as the base shape for the model. In the embodiment of FIG. 2, the base shape of the model is spherical shape. In alternative embodiments, other shapes may be used, such as cuboid shapes, ovoid shapes, paraboloid shapes, and polyhedrons as well as irregular shapes. Preferably, the base shape of the model is selected to generally follow the shape of the molecule of the liquid system. For example, molecules having an elongated shape can be encompassed by a more elongated three-dimensional as the base shape for the model, such as an ovoid, paraboloid, cylinder, etc.

Dividing the system into a device region and a surrounding lead region, the device region and the lead region can be treated separately in solving quantum equations and determining parameters. The parameter values which are calculated separately for the device region 18 (e.g., $P_d$) and the lead region ($P_l$) can then be added to arrive at a total value for the parameter ($P_{total}$) for the system (See, e.g., equation (1)).

$$P_d + P_l = P_{total} \quad (1)$$

Partitioning the system into a device region and a lead region enables the system to be analyzed quantum mechanically. One method of analyzing the liquid system model of FIG. 1 is the Non-Equilibrium Green's Function (NEGF) method. The NEGF is the standard approach to model nanoscale open boundary devices, where coherent quantum effects as well as incoherent scattering are present. The NEGF method can be applied to the device region and the lead region separately and then combined to derive properties for the whole system.

The NEGF method requires the solution of the retarded Green's function ($G^R$) and lesser Green's function ($G^<$) in the device to obtain the transmission and the charge density. The key operation of the NEGF method is the inversion of a matrix with the same rank as the device Hamiltonian. However, the solution time and the peak memory usage increases dramatically as the device dimension increases. This is particularly true for spherical leads. For spherical leads, there is a polynomial order 6 relationship between the size, e.g., radius, of the lead and the computation requirements, e.g., inversions, required to analyze the lead quantum mechanically. The computational load (e.g., time and memory) can quickly become intractable with larger radii.

To reduce the computational load of the NEGF method, the recursive Green's function (RGF) may be used. The RGF method is well-known for improving the efficiency of NEGF calculations. It allows solving the transmission and the charge density with only a minimum number of blocks of the $G^R$ matrix. The RGF algorithm divides the device into partitions and solves the relevant $G^R$ blocks recursively starting with a first partition and continuing in forward direction until a last partition is reached. Afterwards the $G^<$ matrix is solved to obtain the charge density.

Figure 3:
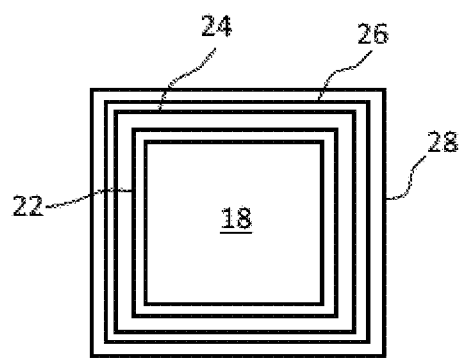
FIG. 3 depicts another embodiment of a model that may be used to model the liquid system of FIG. 1 under open quantum liquid boundary conditions.
Figure 4:
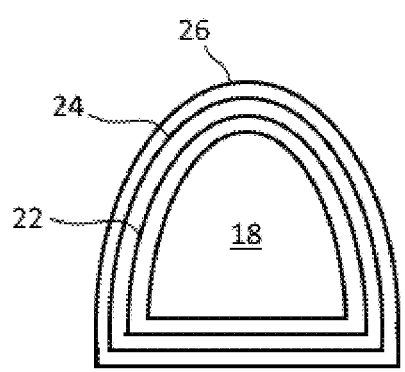
FIG. 4 depicts yet another embodiment of a model that may be used to model the liquid system of FIG. 1 under open quantum liquid boundary conditions.

To enable the RGF algorithm to be applied in the present case, the lead region 20 is further divided into a plurality of partitions (or shells) 22, 24, 26, 28, 30. In the embodiment of FIG. 2 having a spherical base shape, the partitions 22, 24, 26, 28, 30 are each spherical shells 22, 24, 26, 28, 30 which are nested inside each other starting at the device/lead interface 16. FIGS. 3 and 4 show the partitioning of the lead region 20 in models having other base shapes. For example, FIG. 3 shows partitioning of the lead region 20 for a model having a device region 18 that is cuboid shaped, and FIG. 4 shows partitioning of the lead region 20 for a model having a device region that is paraboloid shapes.

The surface area and volume of the shells increase with distance from the device region 18. This means that the shell regions which are farther away from the device have more atoms to consider in calculations than the shell regions which are closer to the device.

However, as can be seen in FIG. 2, dephasing increases as the distance from the device region increases (as indicated by arrows 36, 34). A larger dephasing means that the considered physics is more local in real space. This also means that the amount of non-locality decreases with distance from the device region. Because the lead regions farther away from the device region have less non-locality, the amount of time and memory required to perform the calculations in these regions is less in relation to lead regions which are closer to the device region.

Once the value of a particular parameter has been calculated for each of the shell regions of the lead region, the Green's functions of the respective shell regions ($g_{l1}$, $g_{l2}$ ... $g_{ln}$) can then be combined to arrive at the interface Green's function $g_i$ at the lead/device interface (See, e.g., equation (2)). The device Green's function is then solved with the interface Green's function according to equation (3) and the Keldysh equation. All observables are then deduced from the Green's functions as commonly done in Green's function approaches.

$$g_{li} = (E - H_{li} - H_{li,li-1} g_{li-1} H_{li,li-1})^{-1} \quad (2)$$

$$G^R = (E - H_d - H_{d,l} g_l H_{l,d})^{-1} \quad (3)$$

Any suitable number of layers and/or thickness of layers may be used in the lead region. In one embodiment, the thickness of the respective shells or partitions depends on the distance range of direct molecule-molecule interactions in the liquid/solvent. With this in mind, the thickness of each shell region layer is preferably kept at a minimum to minimize the computational load for each respective shell region.

Figure 5:
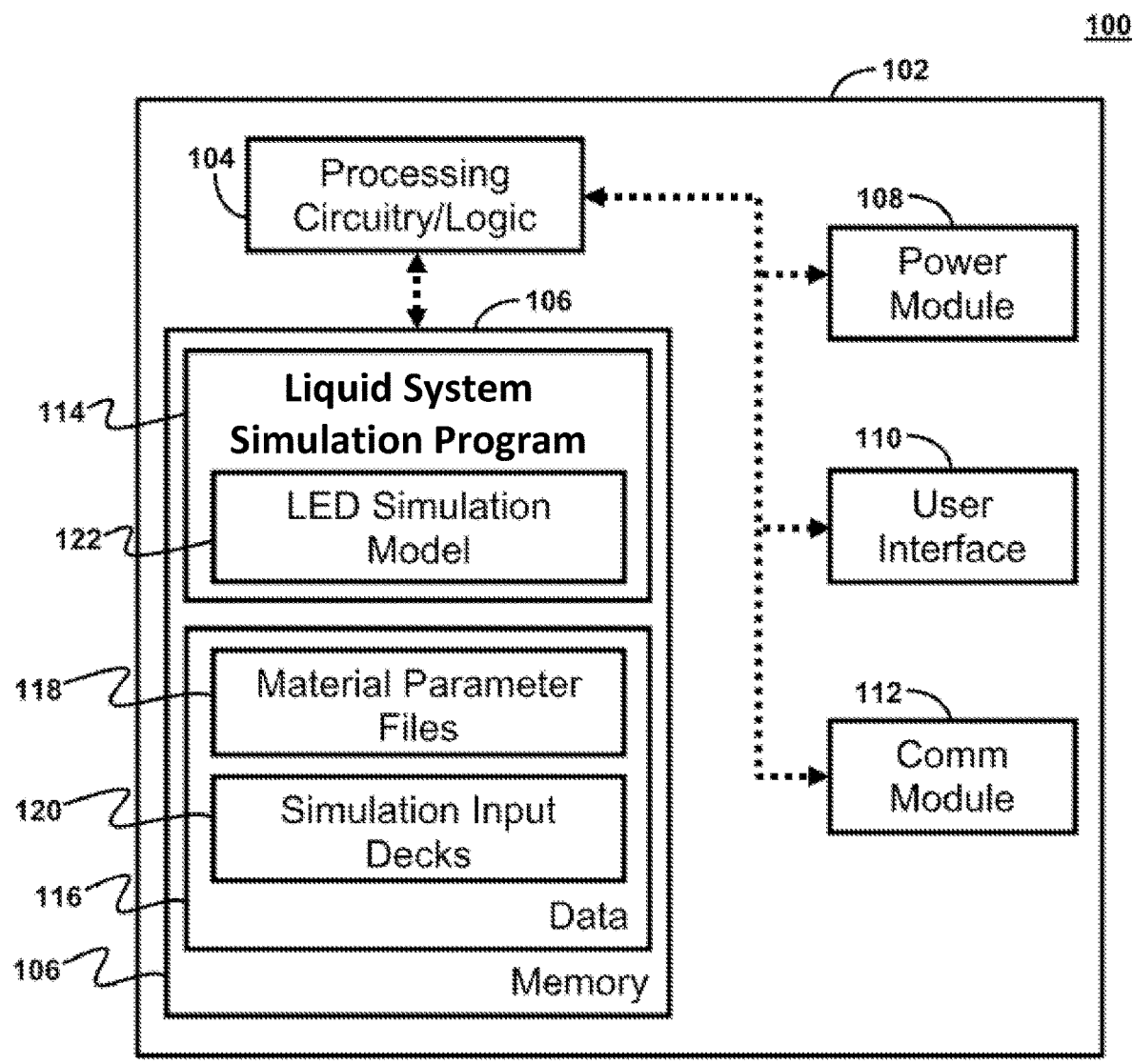
FIG. 5 depicts a block diagram of a nanoelectronic modeling system for generating

FIG. 5 shows a block diagram of an exemplary embodiment of a liquid system simulation system 100 which can be used to generate, analyze, and/or utilize the model for open quantum liquid boundary conditions discussed above in relation to FIGS. 1 and 2. The liquid system simulation system 100 is typically provided in a housing, cabinet, or the like 102 that is configured in a typical manner for a computing device. In one embodiment, the liquid system simulation system 100 includes processing circuitry/logic 104, memory 106, a power module 108, a user interface 110, and a network communications module 112. It is appreciated that the illustrated embodiment of the liquid system simulation system 100 is only one exemplary embodiment of a liquid system simulation system 100 and is merely representative of any of various manners or configurations of a simulation system, personal computer, server, or any other data processing systems that are operative in the manner set forth herein.

The processing circuitry/logic 104 is configured to execute instructions to operate the liquid system simulation system 100 to enable the features, functionality, characteristics and/or the like as described herein. To this end, the processing circuitry/logic 104 is operably connected to the memory 106, the power module 108, the user interface 110, and the network communications module 112. The processing circuitry/logic 104 generally comprises one or more processors which may operate in parallel or otherwise in concert with one another. It will be recognized by those of ordinary skill in the art that a "processor" includes any hardware system, hardware mechanism or hardware component that processes data, signals, or other information. Accordingly, the processing circuitry/logic 104 may include a system with a central processing unit, multiple processing units, or dedicated circuitry for achieving specific functionality.

The memory 106 may be of any type of device capable of storing information accessible by the processing circuitry/logic 104, such as a memory card, ROM, RAM, write-capable memories, read-only memories, hard drives, discs, flash memory, or any of various other computer-readable medium serving as data storage devices as will be recognized by those of ordinary skill in the art. The memory 106 is configured to store instructions including a liquid system simulation program 114 for execution by the processing circuitry/logic 104, as well as data 116 for use by the liquid system simulation program 114.

With continued reference to FIG. 5, the power module 108 of the liquid system simulation system 100 is configured to supply appropriate electricity to the liquid system simulation system 100 (i.e., including the various components of the liquid system simulation system 100). The power module 108 may operate on standard 120 volt AC electricity, but may alternatively operate on other AC voltages or include DC power supplied by a battery or batteries.

The network communication module 112 of the liquid system simulation system 100 provides an interface that allows for communication with any of various devices using various means. In particular, the network communications module 112 may include a local area network port that allows for communication with any of various local computers housed in the same or nearby facility. In some embodiments, the network communications module 112 further includes a wide area network port that allows for communications with remote computers over the Internet. Alternatively, the liquid system simulation system 100 communicates with the Internet via a separate modem and/or router of the local area network. In one embodiment, the network communications module is equipped with a Wi-Fi transceiver or other wireless communications device. Accordingly, it will be appreciated that communications with the liquid system simulation system 100 may occur via wired communications or via the wireless communications. Communications may be accomplished using any of various known communications protocols.

The liquid system simulation system 100 may be operated locally or remotely by a user. To facilitate local operation, the liquid system simulation system 100 may include an interactive user interface 110. Via the user interface 110, a user may access the instructions, including the liquid system simulation program 114, and may collect data from and store data to the memory 106. In at least one embodiment, the user interface 110 may suitably include an LCD display screen or the like, a mouse or other pointing device, a keyboard or other keypad, speakers, and a microphone, as will be recognized by those of ordinary skill in the art. Alternatively, in some embodiments, a user may operate the liquid system simulation system 100 remotely from another computing device which is in communication therewith via the network communication module 112 and has an analogous user interface.

As discussed above, the liquid system simulation system 100 includes a liquid system simulation program 114 stored in the memory 106. The liquid system simulation program 114 is configured to enable to liquid system simulation system 100 to perform calculations of carrier transport properties, quantum properties and/or other observable characteristics (e.g., density, solubility, reactivity, stability, optical spectra, thermal spectra, magnetic properties, susceptibility, and the like) pertaining to one or more simulation models of the system.

As will be discussed in further detail below, the liquid system simulation program 114 improves upon conventional simulation methods by enabling multi-scale simulations that reflect an accurate and quantitative understanding of quantum mechanics-dominated carrier flow in an entire realistically extended complex device. To accomplish this, the liquid system simulation program 114 partitions a model of a system, such as a liquid system, or molecule in solvent system, into a spherical device region and a plurality of spherical cell lead regions. The simulation program is configured to apply any suitable method or algorithm to the partitioned model to derive selected properties for the system being modeled. Examples of such methods and algorithms include NEGF, RGF, nonlocal RGF, DFT, Wannier Functions, etc.

In one exemplary embodiment, the data 116 includes material parameter files 118 and simulation input decks 120. The material parameter files 118 and simulation input decks 120 include data which defines the structure of the nano-electronic device to be simulated, as well as various parameters of the simulation to be performed. The material parameter files 118 and/or simulation input decks 120 describe the structure of the liquid system device at an atomic level, and may include information such as geometries, types of materials, doping levels, crystal structures, and other physical characteristics. Additionally, the material parameter files 118 and/or simulation input decks 120 may describe simulation parameters such as bias voltages, input currents, ambient conditions, physical constants, values for experimentally determined parameters, simulation settings, etc. In some embodiments, the simulation input decks 120 are written in a suitable input deck programming language.

The liquid system simulation program 114 receives the material parameter files 118 and simulation input decks 120 as inputs and utilizes one or more models, algorithms, and/or processes to calculate carrier transport characteristics, or other physical phenomena, of the device defined by the respective material parameter files 118 and simulation input decks 120. In at least one embodiment, the liquid system simulation program 114 is configured to provide the calculated carrier transport characteristics or other physical phenomena in the form of an output file which can be used by another program. In some embodiments, the liquid system simulation program 114 is configured to operate a display device of the user interface 110 to display a graphical depiction of the calculated carrier transport characteristics or other physical phenomena, such as a graph, plot, diagram, or the like.

With continued reference to FIG. 5, the liquid system simulation program 114 includes one or more simulation models for open quantum liquid boundary conditions configured to simulate carrier transport characteristics, quantum properties and/or other physical phenomena of a particular liquid system. In the description of the methods and algorithms described herein, statements that the method or model is performing some task or function refers to a general purpose processor, controller, or the like executing programmed instructions stored in non-transitory computer readable storage media operatively connected to the processor to manipulate data or to operate one or more components in the liquid system simulation system 100 to perform the task or function. Particularly, the processing circuitry/logic 104 above may be such a processor and the executed program instructions may be stored in the memory 106. Additionally, the steps of the methods may be performed in any feasible chronological order, regardless of the order shown in the figures or the order in which the steps are described.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A method for simulating a nanoscale device using a modeling system, the nanoscale device including a liquid system having at least one molecule in a solvent, the method comprising:

receiving model parameters for the liquid system as input to a processor of the modeling system, the model parameters identifying at least one of a type of molecule and a type of solvent to be modeled for the liquid system;

generating a quantum model of the liquid system using the processor, the quantum model partitioning the liquid system into a device region and a lead region, the device region being spherical in shape and encompassing the at least one molecule and a portion of the solvent of the liquid system, the lead region being further partitioned into a plurality of nested shell regions, each nested shell region having a spherical shell shape and encompassing a respective region of the solvent surrounding the device region in the liquid system, the plurality of nested shell regions being arranged in a nested manner starting from a device-lead interface and extending outward from the device region, the device-lead interface defining where the device region meets the lead region; and simulating the nanoscale device using the processor based on the quantum model, the simulating including:

determining a first property of the lead region using Non-Equilibrium Green's Function methods under open boundary conditions for the lead region using the processor, a recursive Green's function algorithm being applied to the plurality of nested shell regions to determine Green's functions for the plurality of nested shell regions of the lead region;

determining the first property of the device region using Non-Equilibrium Green's Function methods using the processor, a Green's function for the device region being determined based on a Green's function for the device-lead interface, the Green's function for the device-lead interface being determined based on the Green's functions for the plurality of nested shell regions of the lead region; and combining the first property of the device region with the first property of the lead region to arrive at a total first property for the liquid system using the processor.

2. The method of claim 1, further comprising:
determining a Hamiltonian for the liquid system; and
determining the Green's function for the device with reference to the Hamiltonian.

3. The method of claim 2, wherein the Hamiltonian is determined using a Wannierization procedure.

4. The method of claim 1, wherein dephasing increases with distance from the device region which results in the nested shell regions that are farther away from the device region having less non-locality than the nested shell regions that are closer to the device region, and
wherein a number of matrix inversions required to solve Green's functions for a given region depends in part on the amount of non-locality in the region.

5. A non-transitory computer readable medium storing a plurality of instructions which are configured to, when executed, cause at least one processor to execute a method for simulating a nanoscale device, the nanoscale device including a liquid system having at least one molecule in a solvent, the method comprising:

receiving model parameters for the liquid system as input to the at least one processor, the model parameters identifying at least one of a type of molecule and a type of solvent to be modeled for the liquid system;

generating a quantum model of the liquid system using the at least one processor, the quantum model including a device region and a lead region, the device region having a shape and encompassing the at least one molecule and a portion of the solvent of the liquid system, the lead region being further partitioned into a plurality of nested shell regions, each nested shell region having a same shell shape and encompassing a respective region of the solvent surrounding the device region in the liquid system, the plurality of nested shell regions being arranged in a nested manner starting from a device-lead interface and extending outward from the device region, the device-lead interface defining where the device region meets the lead region; and simulating the nanoscale device using the at least one processor based on the quantum model, the simulating including:

determining a first property of the lead region using Non-Equilibrium Green's Function methods under open boundary conditions for the lead region using the at least one processor, a recursive Green's function algorithm being applied to the plurality of nested shell regions to determine Green's functions for the plurality of nested shell regions of the lead region;

determining the first property of the device region using Non-Equilibrium Green's Function methods using the at least one processor, a Green's function for the device region being determined based on a Green's function for the device-lead interface, the Green's function for the device-lead interface being determined based on the Green's functions for the plurality of nested shell regions of the lead region; and combining the first property of the device region with the first property of the lead region to arrive at a total first property for the liquid system using the at least one processor.

6. The non-transitory computer readable medium of claim 5, wherein the method further comprises:
determining a Hamiltonian for the liquid system; and
determining the Green's function for the device with reference to the Hamiltonian.

7. The non-transitory computer readable medium of claim 6, wherein the Hamiltonian is determined using a Wannierization procedure.

8. The non-transitory computer readable medium of claim 5, wherein dephasing increases with distance from the device region which results in the nested shell regions that are farther away from the device region having less non-locality than the nested shell regions that are closer to the device region, and wherein a number of matrix inversions required to solve Green's functions for a given region depends in part on the amount of non-locality in the region.

9. A method for simulating a nanoscale device using a modeling system, the nanoscale device including at least one molecule in a solvent, the method comprising:

receiving model parameters for the molecule in the solvent as input to a processor of the modeling system, the model parameters identifying at least one of a type of molecule and a type of solvent to be modeled for the nanoscale device;

generating a quantum model of the molecule in the solvent using the processor, the quantum model including a device region and a lead region, the device region having a shape and encompassing the at least one molecule and a portion of the solvent, the lead region being further partitioned into a plurality of nested shell regions, each nested shell region having a same shell shape and encompassing a respective region of the solvent surrounding the device region, the plurality of nested shell regions being arranged in a nested manner starting from a device-lead interface and extending outward from the device region, the device-lead interface defining where the device region meets the lead region; and simulating the nanoscale device using the processor based on the quantum model, the simulating including:

determining a first property of the lead region using Non-Equilibrium Green's Function methods under open boundary conditions for the lead region using the processor, a recursive Green's function algorithm being applied to the plurality of nested shell regions to determine Green's functions for the plurality of nested shell regions of the lead region;

determining the first property of the device region using Non-Equilibrium Green's Function methods using the processor, a Green's function for the device region being determined based on a Green's function for the device-lead interface, the Green's function for the device-lead interface being determined based on the Green's functions for the plurality of nested shell regions of the lead region; and combining the first property of the device region with the first property of the lead region to arrive at a total first property for the molecule in the solvent using the processor.

10. The method of claim 9, further comprising:
determining a Hamiltonian for the molecule in the solvent; and
determining the Green's function for the device with reference to the Hamiltonian.

11. The method of claim 10, wherein the Hamiltonian is determined using a Wannierization procedure.

12. The method of claim 9, wherein dephasing increases with distance from the device region which results in the nested shell regions that are farther away from the device region having less non-locality than the nested shell regions that are closer to the device region, and wherein a number of matrix inversions required to solve Green's functions for a given region depends in part on the amount of non-locality in the region.

* * * * *